United States Patent
Beck et al.

(10) Patent No.: US 10,444,315 B2
(45) Date of Patent: Oct. 15, 2019

(54) MRI WITH MOTION CORRECTION USING NAVIGATORS ACQUIRED USING A DIXON TECHNIQUE

(71) Applicant: KONINKLIJKE PHILIPS N.V., Eindhoven (NL)

(72) Inventors: Gabriele Marianne Beck, Eindhoven (NL); Tim Nielsen, Eindhoven (NL); Arjan Willem Simonetti, Einhoven (NL); Gwenael Henri Herigault, Eindhoven (NL); Mathijs Visser, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 505 days.

(21) Appl. No.: 14/377,213

(22) PCT Filed: Feb. 4, 2013

(86) PCT No.: PCT/IB2013/050929
§ 371 (c)(1),
(2) Date: Aug. 7, 2014

(87) PCT Pub. No.: WO2013/118040
PCT Pub. Date: Aug. 15, 2013

(65) Prior Publication Data
US 2015/0323637 A1   Nov. 12, 2015

Related U.S. Application Data

(60) Provisional application No. 61/596,772, filed on Feb. 9, 2012.

(30) Foreign Application Priority Data

Feb. 9, 2012 (EP) .................................... 12154672

(51) Int. Cl.
*G01R 33/565* (2006.01)
*A61B 5/055* (2006.01)
(Continued)

(52) U.S. Cl.
CPC ........ *G01R 33/56509* (2013.01); *A61B 5/055* (2013.01); *G01R 33/34* (2013.01);
(Continued)

(58) Field of Classification Search
None
See application file for complete search history.

(56) References Cited

U.S. PATENT DOCUMENTS 5,539,312 A   7/1996 Fu
6,184,682 B1   2/2001 Ehman
(Continued)

FOREIGN PATENT DOCUMENTS

WO   2012073159 A2   6/2012

OTHER PUBLICATIONS

Huo, Donglai et al "Turboprop IDEAL: A Motion Resistant Fat-Water Separation Technique" Magnetic Resonance in Medicine, vol. 61, Dec. 2008 pp. 188-195.
(Continued)

*Primary Examiner* — Amelie R Gillman (57) ABSTRACT

At least a portion of a body (10) is placed in a main magnetic field Bo within the examination volume of a MR device. The portion of the body (10) is subject to an imaging sequence including one or more RF pulses and switched magnetic field gradients to acquire imaging signals. The portion of the body (10) is subject to a navigator sequence applied at least once before, during, or after the imaging sequence. The navigator sequence includes one or more RF pulses and switched magnetic field gradients controlled to acquire navigator signals with a single-point or multi-point Dixon
(Continued)

technique. Translation and/or rotation and/or shear data reflecting motion of the body are derived from the navigator signals during the acquisition of the imaging signals. The translation and/or rotation and/or shear data are used for adapting the imaging sequence and/or for motion correction during reconstruction of an MR image.

11 Claims, 3 Drawing Sheets

(51) Int. Cl.
 *G01R 33/385* (2006.01)
 *G01R 33/34* (2006.01)
 *G01R 33/48* (2006.01)
 *G01R 33/567* (2006.01)

(52) U.S. Cl.
 CPC ....... *G01R 33/385* (2013.01); *G01R 33/4828* (2013.01); *G01R 33/5673* (2013.01); *G01R 33/5676* (2013.01)

(56) References Cited

U.S. PATENT DOCUMENTS

| | | | | |
|---|---|---|---|---|
| 6,958,605 | B2 | 10/2005 | Dale | |
| 7,358,732 | B2 | 4/2008 | Kouwe | |
| 2003/0153826 | A1* | 8/2003 | Jack | A61B 5/055 600/410 |
| 2007/0265520 | A1* | 11/2007 | Posse | A61B 5/055 600/410 |
| 2008/0054899 | A1* | 3/2008 | Aksoy | G01R 33/5611 324/307 |
| 2010/0127702 | A1* | 5/2010 | Greiser | G01R 33/3875 324/309 |
| 2010/0271023 | A1* | 10/2010 | Deimling | G01R 33/3415 324/309 |
| 2011/0254547 | A1* | 10/2011 | Reeder | G01R 33/4828 324/309 |
| 2012/0049845 | A1* | 3/2012 | Bito | G01R 33/485 324/309 |
| 2013/0197347 | A1* | 8/2013 | Moghari | A61B 5/7207 600/410 |

OTHER PUBLICATIONS

Simonetti, A.W. et al "Image-Based Weighted B0 Shimming using a fast Multi-Echo DIXON Technique: Feasibility for Abdominal Imaging", Proceedings of the International Society for Magnetic Resonance in Medicine, May 2011, vol. 19, Apr. 2011, pp. 2718/.
Kellman, P. et al "Improved Cardiac Shim using Field Map Estimate from Multi-Echo Dixon Method", Proceedings of the International Society for Magnetic Resonance in Medicine, vol. 17, Apr. 2009, pp. 4522.
Keupp, Jochen et al "Intrinsic Field Homogeneity Correction in Fast SPin Echo based Amide Proton Transfer MRI", Proceedings of the International Society for Magnetic Resonance in Medicine, 2012, vol. 20, pp. 4185.
Boernert, Peter et al "Water/Fat Resolved WHole-Heart Dixon Coronary MRA: An Initial Comparison", Proceedings of the International Society for Magnetic Resonance in Medicine, vol. 20, 2012, pp. 316.
Yun, Jiang et al "Self-Navigated Ideal Water-Fat Separation with Variable K-Space Averaging", Biomedical Imaging, 2009, pp. 121-124.
Josephs, O. et al "Reducing Ghosting in EPI using Trajectory based Reconstruction with Doxon Method Fat Suppressed Navigator Echoes at 7T", Proceedings of the International Society for Magnetic Resonance in Medicine, 2010, vol. 18, pp. 5058.
Nguyen, Thanh D. et al "Direct Monitoring of Coronary Artery Motion with Cardiac Fat Navigator Echoes", Magnetic Resonance in Medicine, vol. 50, No. 2, Jul. 2003, pp. 235-241.
Feng, Yanqiu, et al "Affine Motion Compensation with Improved Reconstruction in Propeller MRI", 2009 IEEE Engineering in Medicine and Biology Society, pp. 2680-2683.
Brau, A.C. et al "Accelerated IDEAL Water-Fat Separation Techniques for Single- and Multi-Coil Applications", Proceedings of the International Society for Magnetic Resonance in Medicine, 2005, vol. 13, pp. 491.
Yu, Huanzhou et al "Single Acquisition Water-Fat Separation: Feasibility Study for Dynamic Imaging" Magnetic Resonance in Medicine, vol. 55, No. 2, Feb. 2006, pp. 413-422.
Zagorchev L., Goshtasby A., Paulsen K, McAllister T., Young S., Weese J. (2011) Manual Annotation, 3-D Shape Reconstruction, and Traumatic Brain Injury Analysis. In: Liu T., Shen D., Ibanez L., Tao X. (eds) Multimodal Brain Image Analysis. MBIA 2011 Lecture Notes in Computer Science, vol. 7012. Springer, Berlin, Heidelberg.
Zagorchev L., Meyer C., Stehle T., Kneser R., Young S., Weese J. (2011) Evaluation of Traumatic Brain Injury Patients Using a Shape-Constrained Deformable Model. In: Liu T., Shen D., Ibanez L., Tao X. (eds) Multimodal Brain Image Analysis. MBIA 2011. Lecture Notes in Computer Science, vol. 7012. Springer, Berlin, Heidelberg.

* cited by examiner

MRI WITH MOTION CORRECTION USING NAVIGATORS ACQUIRED USING A DIXON TECHNIQUE

CROSS-REFERENCE TO PRIOR APPLICATIONS

This application is the U.S. National Phase application under 35 U.S.C. § 371 of International Application No. PCT/IB2013/050929, filed on Feb. 4, 2013, which claims the benefit of U.S. Provisional Patent Application No. 61/596,772, filed on Feb. 9, 2012 and European Patent Application No. 12154672.5, filed on Feb. 9, 2012. These applications are hereby incorporated by reference herein.

FIELD OF THE INVENTION

The present invention relates to the field of magnetic resonance (MR). It finds particular application in conjunction with MR imaging methods and MR devices for diagnostic purposes, and will be described with particular reference thereto.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field ($B_0$ field) whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field, also referred to as $B_1$ field) of defined frequency (so-called Larmor frequency, or MR frequency). From a macroscopic point of view the distribution of the individual nuclear spins produces an overall magnetization which can be deflected out of the state of equilibrium by application of an electromagnetic pulse of appropriate frequency (RF pulse) while the magnetic field extends perpendicular to the z-axis, so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of one or more receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, switched linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The MR signal data obtained via the RF coils corresponds to the spatial frequency domain and is called k-space data. The k-space data usually includes multiple lines acquired with different phase encoding. Each line is digitized by collecting a number of samples. A set of k-space data is converted to a MR image by means of Fourier transformation.

In a variety of MRI applications, motion of the examined object (the patient) can adversely affect image quality. Acquisition of sufficient MR signals for reconstruction of an image takes a finite period of time. Motion of the object to be imaged during that finite acquisition time typically results in motion artifacts in the reconstructed MR image. In conventional MR imaging approaches, the acquisition time can be reduced to a very small extent only, when a given resolution of the MR image is specified. In the case of medical MR imaging, motion artifacts can result for example from cardiac and respiratory cyclic motion, and other physiological processes, as well as from patient motion resulting in blurring, misregistration, deformation and ghosting artifacts.

Prospective motion correction techniques such as the so-called navigator technique have been developed to overcome problems with respect to motion by prospectively adjusting the imaging parameters, which define the location and orientation of the volume of interest within the imaging volume. In the image navigator technique hereby, a set of navigator signals is acquired at low-resolution from a spatially restricted volume, for example a navigator beam that crosses the diaphragm of the examined patient. For registering the navigator signals, so-called 2D RF pulses or 90 degree and 180 degree cross slab spin echo signals may be used. These excite the spatially restricted navigator volume in the form of a pencil beam, which is read out using a gradient echo. Other ways to detect the motion-induced momentary position of the volume of interest is the acquisition of two-dimensional sagittal slices that are positioned at the top of the diaphragm, or the acquisition of three-dimensional low-resolution data sets. The respective navigator volume is interactively placed in such a way that a displacement value indicating the instantaneous position of the anatomical feature to be imaged can be derived from the acquired navigator signals and used for motion correction of the volume of interest in real time. For example, the navigator technique is used for minimizing the effects of breathing motion in body and cardiac exams where respiratory motion can severely deteriorate the image quality. Gating as well as prospective and also retrospective motion compensation based on the navigator signals has been introduced to reduce these artifacts. Moreover, the navigator signals can be used to prospectively align several scans in an examination. After acquisition of the navigator signals subsequent imaging signals are acquired with the detected motion compensated for, reorientating the stack of image slices and collecting data during motion free time intervals. Finally a MR image is reconstructed from the acquired imaging signals.

As an example the navigator signal used in current coronary or renal MR angiography applications is typically the above-mentioned signal from a pencil beam shaped volume oriented through the diaphragm. Because the respiratory movements of the diaphragm and the heart and kidneys are correlated, the diaphragmatic navigator technique can be used to suppress respiratory motion artifacts in free-breathing coronary and renal MR angiography. However, the sensitivity and specificity of the diaphragmatic navigator approach in detecting stenoses of the coronary and renal arteries appears disappointing. One major factor is the diaphragmatic navigator itself which does not directly monitor the motion of the coronary and renal arteries. This consequently limits the effectiveness for suppressing motion artifacts.

Recently, navigator techniques are also used to prospectively detect and correct for head, prostate and joint motion. Therein coronal, sagittal and transverse localization slices or a 3D low resolution localization slab are acquired to detect translational and rotational motion. Since the afore-described image navigator technique extends acquisition time, the detection of motion and respiratory states (like breath holds) may be achieved alternatively by external motion sensors (like optical and respiratory sensors) or k-space navigators (FNAV, ONAV, cloverleaf navigator). In case motion is detected or a respiratory state is reached, an image navigator is applied to prospectively adapt the imaging stack. Hence in general, a navigator can be applied in case motion is detected (e. g. head motion), a motion state is reached (e. g. end expiration breath hold) or in general interleaving navigators with the acquisition (e. g. free breathing motion).

The paper 'Turboprop IDEAL: a motion resistant fat-water separation technique' in MRM 61(2009)188-195 by D. Huo et al. discloses a motion resistant water-fat separation technique (TP-IDEAL). This known technique aims at avoiding motion artefcats in water-fat separation. This is achieved by averaging shift and rotation to avoid misregistration between the k-space blades in the Propeller acquisition.

SUMMARY OF THE INVENTION

To improve navigator-controlled MR angiography and other MR imaging techniques in which moving portions of the human body are to be imaged, it is necessary to obtain direct and accurate measurements of the relevant motion.

From the foregoing it is readily appreciated that there is a need for an improved MR imaging method. It is consequently an object of the invention to enable MR imaging with reliable motion detection and high image quality.

In accordance with the invention, a method of MR imaging of at least a portion of a body placed in a main magnetic field $B_0$ within the examination volume of a MR device is disclosed. The method comprises the following steps:
  subjecting the portion of the body to an imaging sequence comprising one or more RF pulses and switched magnetic field gradients for acquiring imaging signals;
  subjecting the portion of the body to a navigator sequence applied at least once before, during, or after the imaging sequence, the navigator sequence comprising one or more RF pulses and switched magnetic field gradients controlled in such a manner that navigator signals are acquired by means of a single-point or multi-point Dixon technique;
  deriving translation and/or rotation and/or shear data from the navigator signals, which translation and/or rotation and/or shear data reflect motion occurring within the portion of the body;
  reconstructing a MR image from the imaging signals, wherein the translation and/or rotation data are used for adapting the imaging sequence and/or for motion correction during reconstruction of the MR image.

According to the invention, a navigator sequence is applied at least once in an imaging sequence. Motion occurring within the imaged body portion is compensated for throughout the scan. A navigator sequence within the meaning of the invention is generally a scanning sequence which can be used for determining and acquiring translation and/or rotation and/or shear data. By means of the navigator sequence typically low-resolution data of a one-, two-, or three-dimensional volume is acquired for measuring a rotation of an anatomic feature about at least one coordinate axis, and/or a translation of the respective anatomic feature along at least one coordinate axis. The translation and/or rotation data and/or shear is used either for adapting the imaging sequence. Adapting the imaging sequence means, for example, adapting the position and/or orientation and/or shear of an image slice or any other two- or three-dimensional imaging volume within the body of the patient during the acquisition of the imaging signals. Adapting the imaging sequence includes adaptations in the gradients to compensate for for affine motion. Moreover, a more general motion model may be used for retrospective correction of the acquired imaging signals in order to reduce motion-induced blurring or distortion in the reconstructed MR image. Insofar the method of the invention coincides with the conventional navigator approach.

According to the per se known Dixon technique, the spectral difference between fat and water spins are made use of for the purpose of separating MR signals emanating from water containing tissue and MR signals emanating from fat tissue. In Dixon-type imaging, typically two acquisitions are repeated with different echo times, wherein the fat magnetization in the second acquisition is out of phase relative to the first acquisition at the respective echo times. Separate and distinct water and fat maps are obtained by simple addition or subtraction of the complex MR signals. In general, a $B_0$ field map, a water image and a fat image is obtained by means of a multi-point Dixon sequence.

According to the invention, a single- or multi-point Dixon sequence is applied for acquiring the navigator signals. As mentioned above, the navigator signals are typically read out in conventional navigator techniques by using a single gradient echo. According to the invention, when using the multi-point Dixon sequence, at least one extra echo signal (or an extra partial echo signal) is acquired for obtaining additional information.

In single-point Dixon a single echo signal is acquired at a specific echo time and a water and fat map are reconstructed therefrom. However, in case of single-point Dixon no $B_0$ information is gained.

In case of a multi-point Dixon technique a water navigator, a fat navigator and a $B_0$ navigator can be reconstructed from the navigator signals. These different navigators can then be used for a (preferably automated) segmentation in order to obtain a direct and accurate measurement of the relevant motion. For example, the fat navigator can be applied to the renal arteries and imaging of the kidneys, or the ventricle walls in coronary MR angiography in order to directly monitor breathing related motion in the region of interest. Hereby blood motion does not complicate the extraction of the translation and/or rotation data from the navigator signals. The fat navigator is particularly useful for direct monitoring of renal and coronary artery motion or kidney motion because fat typically surrounds the renal and coronary arteries and the kidneys and moves together with them. Hence, the fat navigator can be incorporated in the motion determination routine according to the invention, thereby improving the precision and robustness of the motion description in the imaged region for adapting the imaging sequence and/or for retrospective motion correction.

It has to be noted that the separate water and fat signals comprised in the navigator signals provide complementary information about the motion of the anatomic feature of interest, such that the combined water and fat navigators can be used according to the invention for an improved segmentation and motion description. In accordance with the invention, the translation and/or rotation data can thus be derived from the water signals and the fat signals taken alone or in combination.

According to a preferred embodiment of the invention, the imaging signals are acquired by means of a single-point or multi-point Dixon technique as well, wherein a water image and a fat image are reconstructed from the imaging signals. Since both water and fat signals are taken into account in the navigator technique according to the invention, a better segmentation of relevant structures and hence a more precise motion estimation is achieved.

The acquisition of navigator signals by means of a Dixon-technique is preferable combined with other ways to acquire navigator signals, such as so-called k-space navigator or navigator signals that are generated by external motion sensors, e.g. by way of a camera that trackes patient (respiratory) motion. Notably, k-space navigator rely on inconsistencies in k-space data. Motion may be monitored by means of k-space navigators or by way of external sensors at a relatively high rate and when motion is detected to exceed a pre-set threshold, then navigator signals are acquired by way of a Dixon technique. Thus, the acquisition of navigator signals by way of the Dixon technique is interleaved by acquisition of the k-space navigators or navigators from the external sensors. The latter navigators require a shorter acquisition time than the Dixon-navigators, so the motion can be tracked at a higher rate by the k-space navigators or the external sensors. Only, when motion is detected that exceeds the pre-set threshold, Dixon-navigators are acquired. In this way high rate motion tracking is combined with the advantages of the Dixon-navigators while achieving a relatively short acquisition time of the navigator signals. The reduced signal acquisition time alternatively allows a three-dimensional Dixon technique, e.g. in that several navigators in three mutual transverse directions are aquired that represent volumetric motion for water and fat regions separately. This enables correction for volumetric motion.

In accordance with another preferred embodiment of the invention, a $B_0$ map indicating spatial (and temporal) variations of the main magnetic field is extracted from the navigator signals. The extraction of the $B_0$ map hereby is in so far advantageous as motion induces changes in the spatial variation of the main magnetic field $B_0$. Motion-correlated $B_0$ variations can generally be observed at all main magnetic field strengths, but they have a particularly adverse effect on image quality at high $B_0$ fields (3 Tesla or more). As mentioned above, a $B_0$ field map can be obtained together with the water signals and the fat signals by means of the multi-point Dixon sequence which is used as the navigator sequence according to the invention. This $B_0$ navigator can be used advantageously for adapting the shim settings of the MR device during acquisition of the imaging signals. In this way, motion-induced changes in the $B_0$ field distribution can be compensated for. Even if no motion is detected in the specified field of view, motion occurring outside the field of view may cause $B_0$ changes that can be detected with this type of navigator. For example, at ultra-high field strengths (7T) breathing induced $B_0$ changes may cause image degradation in the head region (where no motion occurs). Interleaved image navigators according to the invention can depict those $B_0$ changes and enable appropriate compensation or correction. Other types of navigators (for example k-space navigators) can be combined with the technique of the invention and allow to detect $B_0$ changes and to trigger an image navigator. Moreover, the time-dependent $B_0$ map can be used for retrospectively correcting the MR image in the image reconstruction step.

Since a water map, a fat map, and a $B_0$ map can be reconstructed from the navigator signals acquired according to the invention, these maps can be used for segmentation in order to derive a water region and a fat region within the navigator volume. The water region and the fat region are regions within the navigator volume that contain mainly water and fat tissue respectively. On this basis it is possible to determine shim settings that maximize the $B_0$ homogeneity either in the water region or in the fat region. It is also possible to determine the shim settings in such a manner that a compromise is found that provides a decent $B_0$ homogeneity in both the water region and the fat region.

According to yet another embodiment of the invention, the MR frequency ($F_0$) can be derived automatically from the $B_0$ map and the MR device can be controlled accordingly, for example by setting the frequency generator of the MR device to the derived frequency value. Since the $B_0$ map is obtained from the navigator signals according to the invention, the correct MR frequency for acquiring a diagnostic MR image from a specified region can be derived in a straight-forward manner. Notably, the Dixon technique to acquire the navigator signals also provides information on main ($B_0$) field homogeneity as well as on which regions in the body of the patient that contain predominantly water or fat, respectively. That is, on the basis of the Dixon-navigators, the user may select areas that (i) contain predominantly water and (ii) have a high degree of main field ($B_0$) homogeneity. From magnetic resonance signals from this selected region an accurate absolute value of the water resonance frequency is obtained that can be used for accurate tuning of the RF-system of the magnetic resonance examination system. Further, the determination of the absolute water resonance frequency can be updated during imaging because the Dixon navigators are acquired repeatedly. The selection of an optimal box-shaped volume for accurate determination of the MR frequency (i.e. the water resonance frequency) is mentioned per se in the international application WO 2012073159 A2.

The method of the invention described thus far can be carried out by means of a MR device including at least one main magnet coil for generating a main magnetic field within an examination volume, a number of gradient coils for generating switched magnetic field gradients in different spatial directions within the examination volume, at least one RF coil for generating RF pulses within the examination volume and/or for receiving MR signals from a body of a patient positioned in the examination volume, a control unit for controlling the temporal succession of RF pulses and switched magnetic field gradients, and a reconstruction unit for reconstructing MR images from the received MR signals. The method of the invention is preferably implemented by a corresponding programming of the reconstruction unit and/or the control unit of the MR device.

The method of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION

Figure 1:
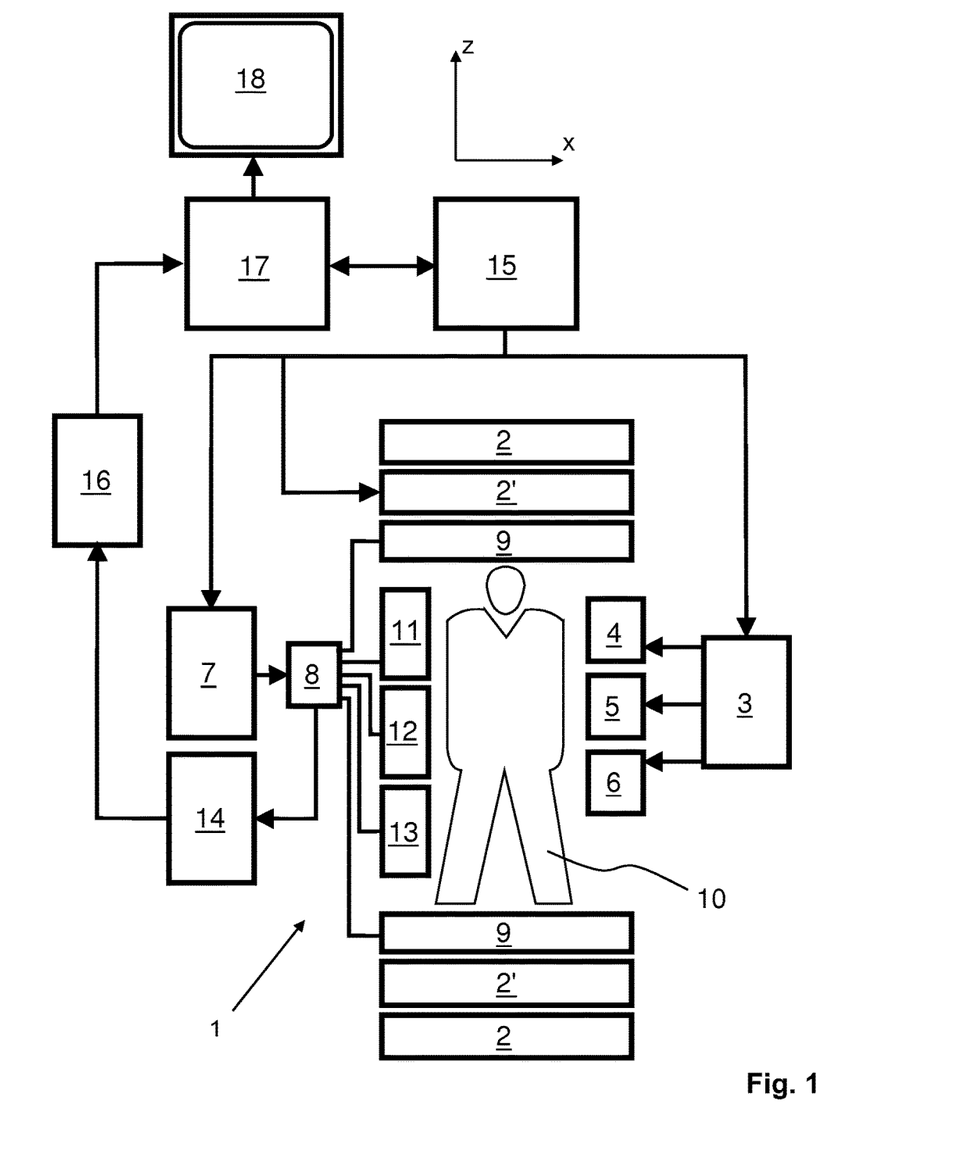
FIG. 1 shows a MR device for carrying out the method of the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$, and—where applicable—$3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

Most specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a body RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the body RF coil 9.

For generation of MR images of limited regions of the body 10 by means of parallel imaging, a set of local array RF coils 11, 12, 13 are placed contiguous to the region selected for imaging. The array coils 11, 12, 13 can be used to receive MR signals induced by body-coil RF transmissions.

The resultant MR signals are picked up by the body RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the current flow through the shimming coils 2' as well as the gradient pulse amplifier 3 and the transmitter 7 to generate any of a plurality of MR imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, such like SENSE or SMASH. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

Figure 2:
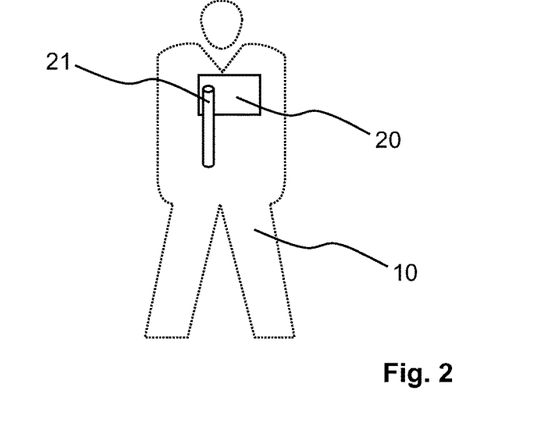
FIG. 2 schematically shows the positions of the volume of interest and the navigator volume within the body of the patient.

FIG. 2 shows the positions of a spatially restricted volume of interest 20 and a navigator volume 21 within the body 10 according to the invention. The per se known navigator technique enables the excitation of nuclear magnetization and the acquisition of corresponding navigator signals within the spatially restricted pencil beam shaped navigator volume 21. FIG. 2 illustrates an application, in which imaging signals are acquired from volume of interest 20 including, for example, the heart of the patient. To detect the breathing state of the patient, the high difference of the amplitude of the MR signal between the lung and the diaphragm suggests ideally placing the navigator volume 21 over the diaphragm/lung interface. According to the invention, navigator signals are acquired from the navigator volume 21 by means of a single- or multi-point Dixon technique. The corresponding navigator sequence is generated interleaving with the imaging sequence which is used to acquire imaging signals from the volume of interest 20. Affine motion transformations including translation and/or rotation data are derived from the navigator signals. This affine motion transformations reflect the breathing motion of the patient and are used for adapting the imaging sequence, for example by changing the position and/or orientation of the volume of interest 20 within the body 10 corresponding to the detected breathing state or by adapting the used gradient strength. Moreover, the motion transformation data can be used for retrospective motion correction during reconstruction of a MR image acquired from the volume of interest 20.

Figure 3:
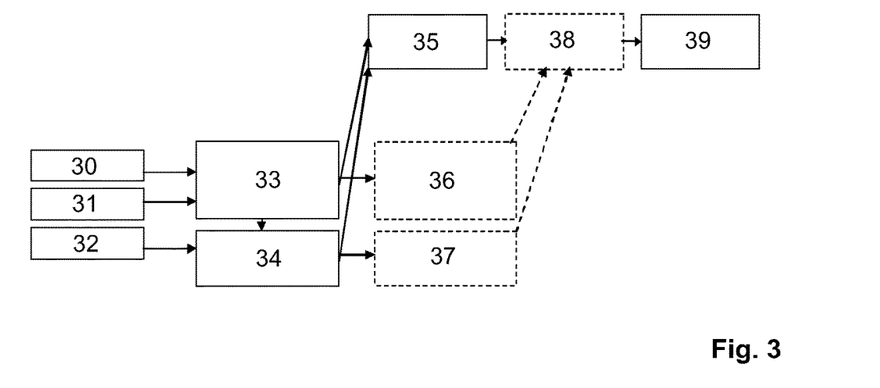
FIG. 3 shows a block diagram schematically illustrating the method of the invention.

The block diagram in FIG. 3 illustrates the method of the invention in more detail. Since the navigator signals are acquired by means of a Dixon technique, actually three navigators are available, namely a water navigator 30, a fat navigator 31, and a $B_0$ navigator 32. The water and fat navigators 30, 31 are actually low resolution water and fat maps respectively, which are reconstructed from the low resolution one-, two-, or three-dimensional navigator signals. The water navigator 30 and the fat navigator 31 are used according to the invention to allow for a high quality segmentation and determination of relevant motion in the volume of interest 20. To this end, the water navigator 30 and the fat navigator 31 are used in a combined fashion for prospective motion description in a method step 33. In this step, affine motion transformations like translation and/or rotation data are derived from the navigators 30, 31. The $B_0$ navigator 32 is used in method step 34 for adapting the shim settings of the MR device 1 accordingly and for adapting the MR frequency of the MR device 1. The translation and/or rotation data derived in step 33 are applied in method step 34 as well in order to adapt the shim settings according to the position and orientation of the volume of interest 20 that may have changed due to the detected motion. In step 35 the portion of the body 10 is subjected to the imaging sequence for acquiring imaging signals from the volume of interest 20. The parameters of the imaging sequence are adapted according to the affine motion transformations like translation and/or rotation derived in step 33. Moreover, the MR frequency and the shim settings applied during the image acquisition step 35 are adapted on the basis of the $B_0$ map. The imaging sequence is adapted, for example by changing the position and orientation of the volume of interest 20 according to the detected breathing state and/or according to the detected change in the motion state. Optionally, the derived affine motion transformation including translation and/or rotation data are used in a step 36 for collecting information for retrospective motion correction. In a similar manner, the $B_0$ map is used in a step 37 for collecting information for retrospective correction of $B_0$ inhomogeneities. This information is used in step 38 to actually correct the imaging signals acquired in step 35 as a part of the image reconstruction process. Step 38 may also comprise retrospective realignment of the acquired imaging signals according to the detected motion and $B_0$ field distortions. The final MR image is reconstructed in step 39.

Figure 4:
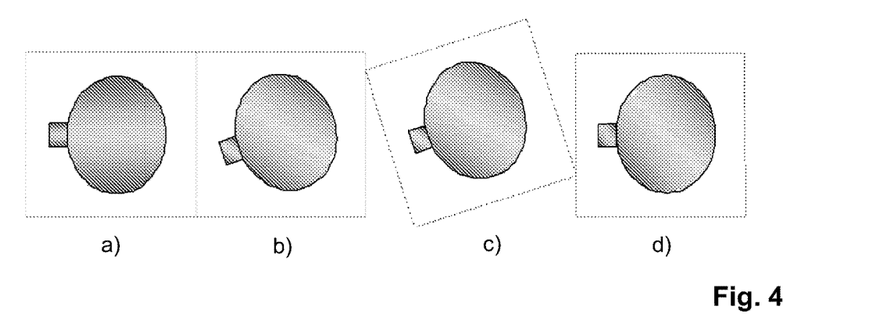
FIG. 4 shows an example of a head application according to the invention that schematically illustrates motion geometric and $B_0$ field corrections.

FIG. 4 illustrates an example of a head application of the invention. FIG. 4a) schematically shows a head image acquired at an initial spatial distribution of the $B_0$ field. The $B_0$ distribution is indicated by the shading in FIG. 4. In FIG. 4b) head motion has occurred which simultaneously caused a change of the $B_0$ field distribution. The water and fat navigators acquired according to the invention are used to determine the translation and rotation of the head and to adapt the field of view accordingly. This is illustrated in FIGS. 4c) and 4d). However, as can be seen in FIG. 4d), the $B_0$ changes are not corrected for by geometrically adapting the field of view. Hence, the $B_0$ navigator of the invention can now be used for adapting the shim settings accordingly and if required for adapting the MR frequency. After a subsequent imaging step a MR image as shown in FIG. 4a) will be obtained again in which the motion-induced geometric changes as well as the changes in the $B_0$ distribution are compensated for.

Figure 5:
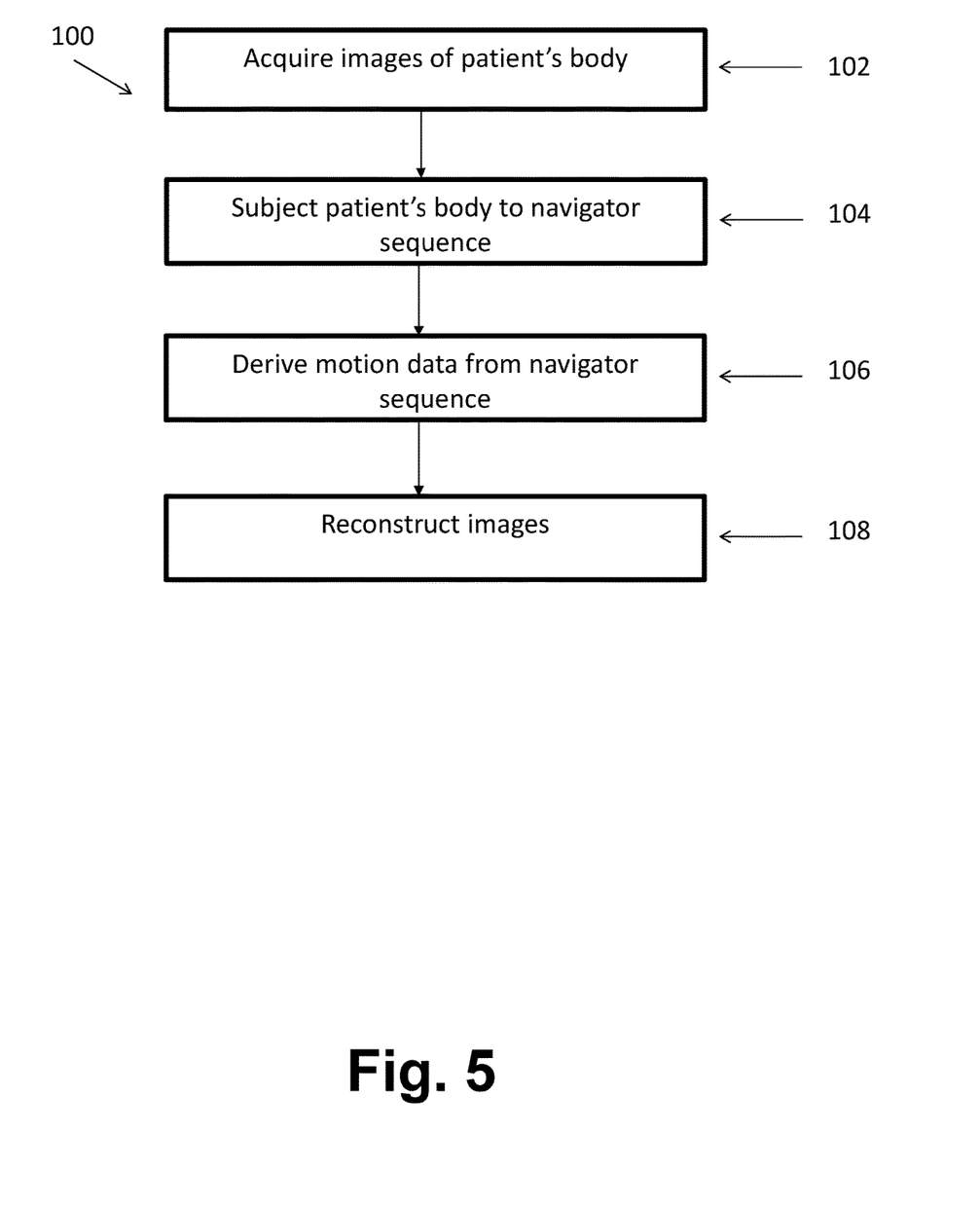
FIG. 5 shows an exemplary flow charts of the device of FIG. 1.

FIG. 5 shows a flow chart showing a method 100 implemented by the MR device 1. At an operation 102, images are acquired of a patient's body. At an operation 104, the patient's body is subjected to a navigator sequence (including water and fat navigator signals). At an operation 106, motion data is derived from the navigator sequence. At an operation 108, MR signals are reconstructed from the derived motion data.

The invention claimed is:

1. A method of magnetic resonance (MR) imaging of at least a portion of a body placed in a main magnetic field $B_0$ within an examination volume of a MR device, the method comprising:
    subjecting the portion of the body to an imaging sequence comprising one or more RF pulses and switched magnetic field gradients for acquiring imaging signals;
    subjecting the portion of the body to a navigator sequence applied at least once before, during, or after the imaging sequence, the navigator sequence including one or more radio frequency (RF) pulses and switched magnetic field gradients controlled so that separate water navigator signals and fat navigator signals are acquired by means of a single-point or multi-point Dixon technique from a navigator volume of the navigator sequence when motion data indicative of motion occurring within the body exceeds a preselected threshold, the motion data being monitored by k-space navigators or one or more external sensors;
    deriving translation and/or rotation and/or shear data from the water navigator signals and the fat navigator signals, wherein the translation and/or rotation and/or shear data reflect the motion occurring within the body;
    reconstructing MR images from the imaging signals,
    wherein the translation and/or rotation and/or shear data are used for adapting the imaging sequence and/or for motion correction during reconstruction of the MR images.

2. The method of claim 1, wherein the imaging sequence is a single-point or multi-point Dixon technique which generates separate water imaging signals and fat imaging signals, and wherein reconstructing the MR images includes reconstructing the water imaging signals into a water image and reconstructing the fat imaging signals into a fat image.

3. The method of claim 1, further including:
    generating a $B_0$ map indicating spatial and/or temporal variations of the main magnetic field using the multi-point Dixon technique; and
    adjusting shim settings of the MR device during acquisition of the imaging signals on the basis of the $B_0$ map.

4. The method of claim 1, further including:
    extracting a $B_0$ map indicating spatial and/or temporal variations of the main magnetic field in regions containing predominantly water using the multi-point Dixon technique; and
    from a homogeneous $B_0$ region containing predominantly water, determining an actual MR resonance frequency of water.

5. The method of claim 4, further including:
    with the $B_0$ map, correcting for the spatial variations of the main magnetic field during the reconstructing of the MR images.

6. A magnetic resonance (MR) device comprising at least one main magnet coil configured to generate a main magnetic field $B_0$ within an examination volume, a plurality of gradient coils configured to generate switched magnetic field gradients in different spatial directions within the examination volume, at least one radio frequency (RF) coil configured to generate RF pulses within the examination volume and to receive MR signals from a body of a patient positioned in the examination volume, a reconstruction processor configured to reconstruct MR images from the received MR signals, and a control processor configured to:
- control the gradient coils and the at least one RF coil to subject a portion of the body to an imaging sequence comprising one or more RF pulses and switched magnetic field gradients for acquiring imaging signals;
- control the gradient coils and the at least one RF coil to subject the portion of the body to a navigator sequence applied at least once before, during, or after the imaging sequence, the navigator sequence comprising one or more RF pulses and switched magnetic field gradients used to acquire Dixon water navigator signals and Dixon fat navigator signals by a single-point or multi-point Dixon technique and to acquire non-Dixon k-space navigator signals when motion data indicative of motion occurring within the body exceeds a preselected threshold, the motion data being monitored by k-space navigators or one or more external sensors;
- derive translation and/or rotation and/or shear data from the Dixon water and fat navigator signals, wherein the translation and/or rotation and/or shear data reflect the motion occurring within the body;
- reconstruct MR images from the imaging signals; and
- use the translation and/or rotation and/or shear data for adapting the imaging sequence and/or for motion correction during the reconstruction of the MR images.

7. A non-transitory computer-readable medium carrying a computer program which controls one or more computers of a magnetic resonance (MR) device to control the MR device to:
- generate an imaging sequence comprising one or more RF pulses and switched magnetic field gradients for acquiring imaging signals;
- generate a Dixon navigator sequence and a non-Dixon k-space navigator sequence in an interleaved manner, the navigator sequences being applied at least once before, during, or after the imaging sequence;
- derive translation and/or rotation and/or shear data from water navigator signals and fat navigator signals acquired by applying the Dixon navigator sequence, wherein the translation and/or rotation and/or shear data reflect motion occurring within a body;
- wherein the water navigator signals and the fat navigator signals are acquired when motion data indicative of the motion occurring within the body exceeds a threshold, the motion data being monitored by non-Dixon k-space navigator signals acquired by applying the non-Dixon k-space navigator sequence or by one or more external sensors;
- reconstruct a MR image from the imaging signals; and
- use the translation and/or rotation and/or shear data for adapting the imaging sequence and/or for motion correction during reconstruction of the MR image.

8. The non-transitory computer-readable medium of claim 7, wherein the computer program controls the one or more computers of a magnetic resonance (MR) device to control the MR device to:
- generate a main field homogeneity map from the Dixon water and fat navigator signals; and
- from regions containing predominantly water and a homogeneous main magnetic field, determine an actual MR frequency of water.

9. A magnetic resonance (MR) device comprising at least one main magnet coil configured to generate a main magnetic field $B_0$ within an examination volume, a plurality of gradient coils configured to generate switched magnetic field gradients in different spatial directions within the examination volume, at least one radio frequency (RF) coil configured to generate RF pulses within the examination volume and to receive MR signals from a body of a patient positioned in the examination volume, a reconstruction processor configured to reconstruct MR images from the received MR signals, and a control processor configured to:
- control the gradient coils and the at least one RF coil to subject a portion of the body to an imaging sequence comprising one or more RF pulses and switched magnetic field gradients for acquiring imaging signals;
- control the gradient coils and the at least one RF coil to generate non-Dixon k-space navigator sequences and Dixon navigator sequences, at least one of the non-Dixon and Dixon navigator sequences being generated at least once before, during, or after the imaging sequence, each Dixon navigator sequence comprising one or more RF pulses and switched magnetic field gradients controlled to acquire Dixon water navigator signals and Dixon fat navigator signals by a single-point or multi-point Dixon technique when motion data indicative of motion occurring within the body exceeds a preselected threshold, the motion data being monitored by k-space navigators or one or more external sensors; and
- derive translation and/or rotation and/or shear data from the Dixon water and fat navigator signals, wherein the translation and/or rotation and/or shear data reflect the motion occurring within the body.

10. The magnetic resonance device of claim 9, wherein the control processor is further configured to:
- correct spatial and/or temporal variations of the main magnetic field in regions of the body portion that are primarily water based on the Dixon water navigator signals;
- correct spatial and/or temporal variations of the main magnetic field in regions of the body portion that are primarily fat based on the Dixon fat navigator signals.

11. A method of magnetic resonance (MR) imaging of at least a portion of a body placed in a main magnetic field $B_0$ within an examination volume of an MR device, the method comprising:
- subjecting the portion of the body to an imaging sequence comprising one or more RF pulses and switched magnetic field gradients for acquiring imaging signals;
- subjecting the portion of the body to a navigator sequence applied at least once before, during, or after the imaging sequence, the navigator sequence comprising one or more RF pulses and switched magnetic field gradients controlled in such a manner that non-Dixon k-space navigator signals and Dixon navigator signals are acquired from a navigator volume, the Dixon navigator signals being acquired using a single-point or multi-point Dixon technique when motion data indicative of motion occurring within the body exceeds a preselected threshold, the motion data being monitored by k-space navigators or one or more external sensors, wherein the Dixon navigator signals include separate water navigator signals and fat navigator signals;
- deriving translation and/or rotation and/or shear data from the water navigator signals and fat navigator signals of the Dixon navigator signals, wherein the translation and/or rotation and/or shear data reflect motion occurring within the body;
- reconstructing MR images from the imaging signals, wherein the translation and/or rotation and/or shear data are used for adapting the imaging sequence and/or for motion correction during the reconstruction of the MR images.

* * * * *